(12) United States Patent
Burg et al.

(10) Patent No.: US 8,961,535 B2
(45) Date of Patent: Feb. 24, 2015

(54) METHOD AND APPARATUS FOR SECURING A GUIDE TUBE

(75) Inventors: Bruce M. Burg, Louisville, CO (US); Brad Jacobsen, Erie, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 104 days.

(21) Appl. No.: 13/280,993

(22) Filed: Oct. 25, 2011

(65) Prior Publication Data
US 2013/0103048 A1 Apr. 25, 2013

(51) Int. Cl.
*A61B 19/00* (2006.01)
*A61B 17/34* (2006.01)

(52) U.S. Cl.
CPC ........... *A61B 19/201* (2013.01); *A61B 17/3439* (2013.01); *A61B 17/3472* (2013.01); *A61B 2019/208* (2013.01)
USPC ....................................................... 606/129

(58) Field of Classification Search
CPC ............. A61B 19/201; A61B 17/3439; A61B 17/3472; A61B 2019/208
USPC .................................. 606/108, 129, 184, 185
See application file for complete search history.

(56) References Cited

U.S. PATENT DOCUMENTS

| | | | | |
|---|---|---|---|---|
| 4,903,707 A * | 2/1990 | Knute et al. | ................... | 600/561 |
| 4,998,938 A | 3/1991 | Ghajar et al. | | |
| 5,054,497 A * | 10/1991 | Kapp et al. | ..................... | 600/561 |
| 5,197,971 A * | 3/1993 | Bonutti | .......................... | 606/192 |
| 5,290,254 A * | 3/1994 | Vaillancourt | ................. | 604/192 |
| 8,504,285 B2 | 8/2013 | Vepsalainen | | |
| 2004/0010190 A1 | 1/2004 | Shahidi | | |
| 2004/0049222 A1* | 3/2004 | Schaeffer et al. | .............. | 606/191 |
| 2008/0051734 A1* | 2/2008 | Bonutti et al. | ................. | 604/264 |
| 2008/0183191 A1 | 7/2008 | Schoepp | | |
| 2008/0269599 A1 | 10/2008 | Csavoy et al. | | |
| 2009/0259230 A1 | 10/2009 | Khadem et al. | | |
| 2009/0306586 A1* | 12/2009 | Ross et al. | .................. | 604/93.01 |
| 2010/0081914 A1 | 4/2010 | Waynik et al. | | |
| 2010/0210939 A1 | 8/2010 | Hartmann et al. | | |
| 2011/0144590 A1* | 6/2011 | Sakai et al. | .............. | 604/167.01 |
| 2011/0184245 A1* | 7/2011 | Xia et al. | ....................... | 600/202 |
| 2012/0158061 A1* | 6/2012 | Koch et al. | ..................... | 606/248 |

FOREIGN PATENT DOCUMENTS

WO WO-9742870 A1 11/1997

OTHER PUBLICATIONS

International Search Report and Written Opinion mailed on Apr. 15, 2013 for PCT/US2012/060540 claiming benefit of U.S. Appl. No. 13/280,993, filed Oct. 25, 2011.

* cited by examiner

*Primary Examiner* — Thomas McEvoy
*Assistant Examiner* — Julie A Szpira
(74) *Attorney, Agent, or Firm* — Harness, Dickey

(57) ABSTRACT

A guide tube is used for guiding an instrument through a hole within tissue of a patient. The guide tube includes a cannula member defining a passage extending therethrough along an axis. The passage is operable to receive the instrument and guide the instrument through the hole within the tissue of the patient. The guide tube also includes an expansion member that is moveably coupled to the cannula member to selectively move radially between a retracted position and an expanded position relative to the axis of the cannula member. The expansion member is at least partially insertable into the hole when the expansion member is in the retracted position. The expansion member is operable to engage with a surface of the hole when the expansion member is in the expanded position.

16 Claims, 2 Drawing Sheets

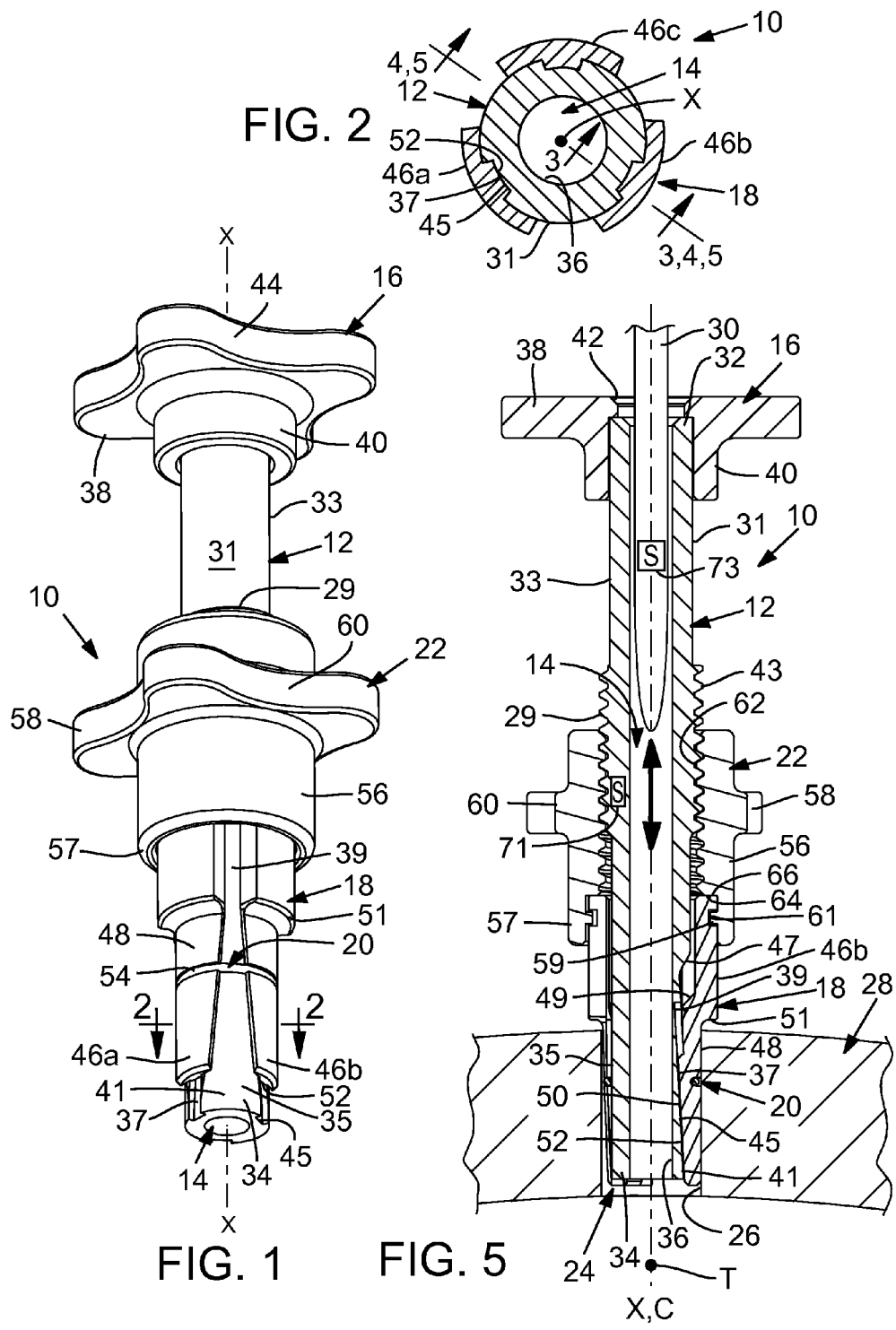

METHOD AND APPARATUS FOR SECURING A GUIDE TUBE

FIELD

The present disclosure relates to a guide tube and, more particularly, to a method and apparatus for securing a guide tube.

BACKGROUND

This section provides background information related to the present disclosure which is not necessarily prior art.

Guide tubes are often used during surgery and other medical procedures for guiding instruments into and out of the patient's body. For instance, neurological probes are often introduced through a patient's skull (cranium) toward a target on the brain. The probe can electrically stimulate the brain tissue for analysis thereof, and then the probe can be removed through the same hole in the skull. A guide tube can be used to maintain a desired trajectory of the probe during insertion and removal from the skull. Similar guide tubes can also be used in other medical procedures as well.

In some specific examples, the guide tube is mounted directly to an outer surface of the patient's skull, and the probe is guided along a surface of the tool to ensure the desired trajectory. In other systems, the patient's head is secured in a desired position, the guide tube is a fixture that remains separate from the patient's body. The probe is operably attached to the fixture, which guides the probe toward and away from the patient.

SUMMARY

This section provides a general summary of the disclosure, and is not a comprehensive disclosure of its full scope or all of its features.

A guide tube used for guiding an instrument through a hole within tissue of a patient is disclosed. The guide tube includes a cannula member defining a passage extending therethrough along an axis. The passage is operable to receive the instrument and guide the instrument through the hole within the tissue of the patient. The guide tube also includes an expansion member that is moveably coupled to the cannula member to selectively move radially between a retracted position and an expanded position relative to the axis of the cannula member. The expansion member is at least partially insertable into the hole when the expansion member is in the retracted position. The expansion member is operable to engage with a surface of the hole when the expansion member is in the expanded position.

A method for engaging a guide tube with a surface of a hole formed in tissue of a patient is also disclosed. The guide tube includes a cannula member defining a passage extending therethrough along an axis and an expansion member that is moveably coupled to the cannula member to selectively move radially between a retracted position and an expanded position relative to the axis of the cannula member. The method also includes inserting the guide tube into the hole while the expansion member is in the retracted position. Furthermore, the method includes selectively moving the expansion member from the retracted position to the expanded position to engage the expansion member with the surface of the hole.

Furthermore, a guide tube for guiding a neurological instrument through a hole formed within a cranium of a patient is disclosed. The hole is defined by an inner surface. The guide tube includes a cannula member defining a passage extending therethrough along an axis. The passage is operable to receive the neurological instrument and guide the instrument through the hole. The guide tube also includes an expansion mechanism that includes a plurality of sections that are slidably attached to a tapered portion of an exterior surface of the cannula member. The plurality of sections are operable to slide on the tapered portion of the exterior surface to thereby move radially relative to the axis between a retracted position and an expanded position. The guide tube also includes a biasing member that is operably coupled to each of the plurality of sections to bias the plurality of sections toward the axis to bias the plurality of sections toward the retracted position. Furthermore, the guide tube includes a retaining mechanism that is threadably attached to the cannula member. The retaining mechanism is operable to threadably advance relative to the cannula member to slide the plurality of sections along the tapered portion of the exterior surface of the cannula member to move the plurality of sections toward the expanded position. The retaining mechanism is also operable to retain the plurality of sections in the expanded position to engage with the inner surface of the hole.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is an isometric view of a guide tube according to various exemplary embodiments of the present disclosure;

FIG. 2 is a section view of the guide tube taken along the line 2-2 of FIG. 1;

FIG. 5 is a section view of the guide tube taken along line 5-5 of FIG. 2, wherein the expansion member is shown in an expanded position and engaged with an inner surface of the bore hole.

Corresponding reference numerals indicate corresponding parts throughout the several views of the drawings.

DETAILED DESCRIPTION

Figure 4:
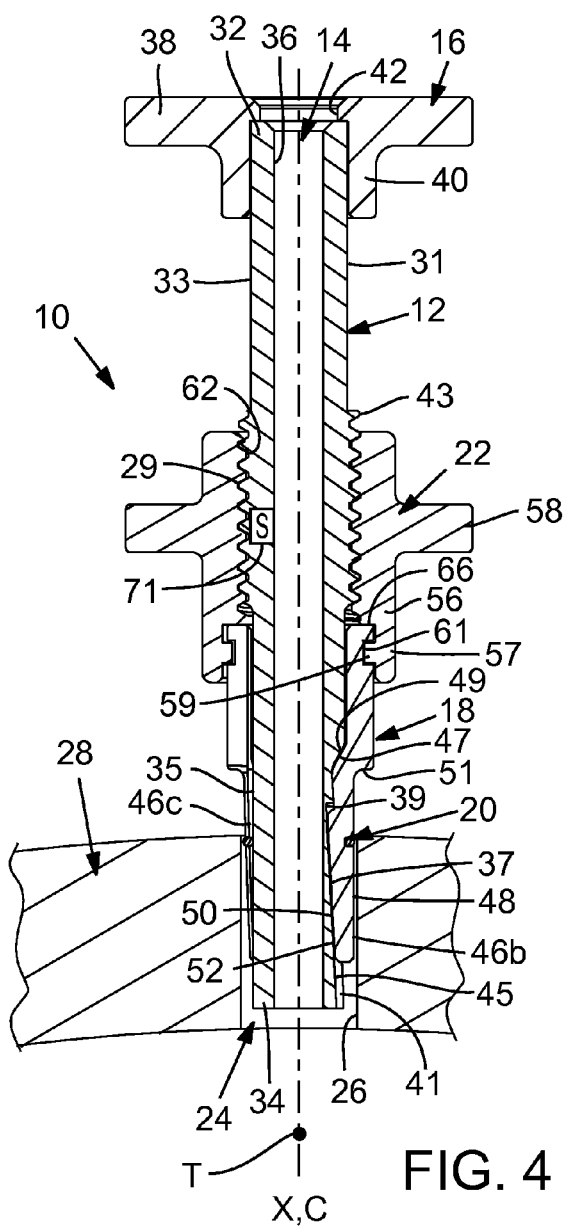
FIG. 4 is a section view of the guide tube taken along line 4-4 of FIG. 2 shown partially inserted in a bore hole within a patient, wherein an expansion member is shown in a retracted position.

Example embodiments will now be described more fully with reference to the accompanying drawings.

Referring initially to FIG. 1, a guide tube 10 (i.e., guide tool) is illustrated according to various exemplary embodiments of the present disclosure. The guide tube 10 can generally include a cannula member 12 defining a passage 14 extending therethrough along a longitudinal axis X. The guide tube 10 can also include a handle member 16 and an expansion member 18 (expansion mechanism) that are operably coupled to opposite ends of the cannula member 12. The expansion member 18 can be moveably coupled to the cannula member 12 to move radially between a retracted position (FIG. 4) and an expanded position (FIG. 5) relative to the axis X of the cannula member 12. The guide tube 10 can further include a biasing member 20 that biases the expansion member 18 toward the retracted position or the expanded position. Furthermore, the guide tube 10 can include a retaining mechanism 22 that can selectively move the expansion member 18 against the biasing load supplied by the biasing member 20, and the retaining mechanism 22 can retain the expansion member 18 in at least one of the retracted and expanded positions.

Thus, as shown in FIGS. 4 and 5, the guide tube 10 can be used to selectively engage with and disengage from a surface 26 (e.g., an inner diameter surface) of a burr hole 24 formed within tissue 28 (e.g., skin, fat, cranial or other bone tissue, etc.). The burr hole 24 can be formed to have a substantially constant width (e.g., diameter) along its axial length (i.e., the hole 24 can be non-tapered).

During use, the expansion member 18 can be moved to the retracted position (FIG. 4) to have a smaller width than the hole 24 such that the guide tube 10 can be partially inserted into the hole 24 and/or removed from the hole 24. Also, the expansion member 18 can be moved to the expanded position (FIG. 5) to engage with the inner surface 26 and to fix the expansion member 18 in position relative to the tissue 28. In this position, the passage 14 in the cannula member 12 can be aligned with the hole 24 in the tissue 28, and an instrument 30 (e.g., a neurological probe 30, etc.) can be moved through the passage 14 of the cannula member 12 along the axis X to move into and out of the hole 24 in the tissue 28. The cannula member 12 can guide this movement of the probe 30 such that the probe 30 moves along a desired trajectory toward and away from a target T within the body.

Various embodiments of the guide tube 10 will now be discussed in detail. Although the guide tube 10 is described in connection with neurological procedures, it will be appreciated that the guide tube 10 could be used in connection with any other medical procedure without departing from the scope of the present disclosure.

Figure 3:
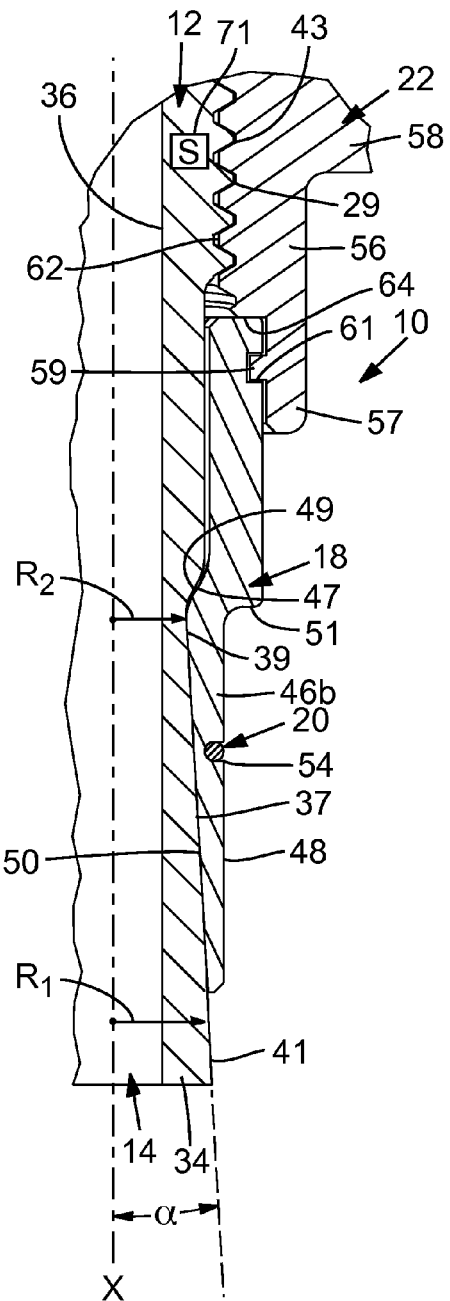
FIG. 3 is an enlarged section view of a distal portion of the guide tube taken along line 3-3 of FIG. 2.

As shown in FIGS. 1-3, the cannula member 12 can be hollow and tubular with a proximal end 32 and a distal end 34. The passage 14 can extend continuously from the proximal end 32 to the distal end 34. The axis X can be substantially straight as shown, or the axis X could be curved in some embodiments. Moreover, in some embodiments, the curvature of the passage 14 could be adjustable due to the construction of the cannula member 12 and/or other portions of the guide tube 10.

The passage 14 can be defined by an inner surface 36, and the inner surface 36 can have a substantially constant diameter for the majority of its longitudinal length. Also, in some embodiments, the inner surface 36 can be tapered along its length.

As shown in FIG. 1, the cannula member 12 can further include an exterior surface 31 having a proximal portion 33, a distal portion 35, and an intermediate portion 29. In some embodiments, the proximal portion 33 of the exterior surface 31 can have a constant width (e.g., diameter) along its axial length. The distal portion 35 can include at least one tapered surface 37 that tapers in width along its axial length. The intermediate portion 29 can be threaded (i.e., can include an outer threading 43).

In some embodiments, the distal portion 35 of the exterior surface 31 of the cannula member 12 can include one or more exterior grooves 45 (FIGS. 1 and 2). The grooves 45 can extend axially (i.e., longitudinally) on the cannula member 12 and can be spaced apart about the axis X (FIG. 2). In the embodiments shown in FIG. 2, there are three grooves 45 evenly spaced apart by 120 degrees about the axis X, but there can be any number of grooves 45 at any angular spacing. The depth of each groove 45 can change gradually along its axial length to define the tapered surface 37. More specifically, the groove 45 can be deeper at a proximal end 39 than at a distal end 41. Thus, the tapered surface 37 can be tapered at an acute angle α relative to the axis X (FIG. 3). The tapered surface 37 can be tapered at any angle α (e.g., approximately three degrees). Also, the tapering of the surface 37 could be such that a distal radius R1 at the distal end 41 is greater than a proximal radius R2 at the proximal end 39.

Furthermore, the cannula member 12 can include one or more shoulders 47 (FIGS. 3-5). The shoulder(s) 47 can be defined at the proximal end 39 of the respective groove 45. As will be discussed, the shoulders 47 can limit movement of the expansion member 18 relative to the cannula member 12.

Exemplary embodiments of the handle member 16 of the guide tube 10 are shown in FIGS. 1, 4, and 5. The handle member 16 can include an upper plate 38 and an attachment portion 40 that are integrally attached. The attachment portion 40 can be hollow and tubular and can be fixed to the proximal end 32 of the cannula member 12. The upper plate 38 can be flat and disc-shaped and can extend perpendicularly from the axis X. The upper plate 38 can also include one or more recesses 44. The recesses 44 can be contoured and spaced about the axis X for improved handling of the guide tube 10. Additionally, the handle member 16 can include an opening (e.g., a through hole) that is centered over the proximal end 32 of the passage 14.

Referring to FIGS. 1, 2, and 3, the expansion member 18 will be discussed in greater detail. The expansion member 18 can include a plurality of sections 46a, 46b, 46c. In the illustrated embodiments, there are three sections 46a, 46b, 46c, but there can be any number of sections 46a, 46b, 46c. Each section 46a, 46b, 46c can be elongate and can include an outer surface 48 and an inner surface 50. The inner surface 50 can include a rail 52 (FIG. 2) that is received within a respective groove 45 of the cannula member 12. Thus, the rail 52 can be tapered relative to the axis X, similar to the respective groove 45. Also, as shown in FIG. 2, the sections 46a, 46b, 46c can be spaced apart circumferentially about the axis X. The outer surface 48 of the sections 46a, 46b, 46c can be substantially smooth or can have a rough texture (e.g., small spikes, knobs, etc.) for engaging the inner surface 26 of the hole 24. However, the outer surface 48 of the sections 46a, 46b, 46c can extend substantially parallel to the axis X.

The rails 52 of the sections 46a, 46b, 46c can axially slide in tandem on the tapered surface 37 of the grooves 45 of the cannula member 12. While sliding, the sections 46a, 46b, 46c can move simultaneously in the axial and radial directions for moving between the expanded position (FIG. 5) and the retracted position (FIG. 4). Specifically, when moving from the retracted position to the expanded position, the sections 46a, 46b, 46c can move toward the distal end 34 and radially outward away from the axis X. In contrast, when moving from the expanded position to the retracted position, the sections 46a, 46b, 46c can move toward the proximal end 32 and radially inward toward the axis X. Because the rails 52 move within the respective grooves 45, this sliding movement can be very smooth and controlled.

It will be appreciated also that the sections 46a, 46b, 46c could include the grooves 45 and the cannula member 12 can include the rails 52 without departing from the scope of the present disclosure. Furthermore, it will be appreciated that the grooves 45 and rails 52 could be interconnected via a dovetail or otherwise keyed against rotation about the axis X.

The inner surface 50 of the sections 46a, 46b, 46c can also include an abutment wall 49 (FIGS. 3-5) that abuts against the respective shoulder 47 of the cannula member 12, for instance, when the sections 46a, 46b, 46c are in the fully retracted position (FIG. 4). This abutment can limit the movement of the sections 46a, 46b, 46c along the axis X toward the proximal end 32.

Furthermore, the sections 46a, 46b, 46c can also include an exterior shoulder 51. The exterior shoulder 51 can be rounded about the axis X. In some embodiments, the width of the guide tube 10 measured at the exterior shoulders 51 can be greater than the width of the burr hole 24 (FIGS. 4 and 5), to thereby limit movement of the guide tube 10 into the burr hole 24.

In addition, the sections 46a, 46b, 46c can each include a groove 54 (FIGS. 1 and 3-5). The grooves 54 can extend circumferentially across the sections 46a, 46b, 46c.

The biasing member 20 can be seen most clearly in FIGS. 1 and 3-5. The biasing member 20 can be a resiliently elastic O-ring that is received within the grooves 54 of the sections 46a, 46b, 46c of the expansion member 18. Positioned as such, the biasing member 20 can remain in resilient tension such that the biasing member 20 biases the sections 46a, 46b, 46c radially toward the axis X. Because of the tapered surface 37, the biasing member 20 also biases the sections 46a, 46b, 46c toward the retracted position.

The retaining mechanism 22 can include a hollow tubular section 56 and a handle section 58 that extends perpendicularly from the tubular section 56. The tubular section 56 can receive the cannula member 12. Specifically, the tubular section 56 can include interior threading 62 that is threadably engaged with the threading 43 of the cannula member 12. The tubular section 56 can also include a cuff 57 that receives and overlaps the proximal, exterior end of the sections 46a, 46b, 46c.

As shown in FIGS. 3, 4, and 5, the cuff 57 can include an annular projection 59 that extends radially inward toward the axis X. The projection 59 can be received within a corresponding annular notch 61 formed within the sections 46a, 46b, 46c to interconnect the retaining mechanism 22 and ensure tandem movement of the retaining mechanism 22 and sections 46a, 46b, 46c as will be discussed. It will be appreciated that the sections 46a, 46b, 46c could include the projection 59 while the retaining mechanism 22 could include the notch 61 without departing from the scope of the present disclosure.

The retaining mechanism 22 can be rotated and threadably advanced in either direction parallel to the axis X. The handle section 58 can include one or more curved recesses 60 that facilitate rotation of the retaining mechanism 22 about the axis X.

As shown in FIGS. 3-5, when the retaining mechanism 22 is threadably advanced toward the distal end 34 of the cannula member 12, a distal abutment surface 64 of the retaining mechanism 22 pushes against a proximal end 66 of the sections 46a, 46b, 46c parallel to the axis X. This causes the sections 46a, 46b, 46c to slide along the tapered surface 37 to move both parallel to the axis X toward the distal end 34 and radially outward toward the expanded position. The threaded engagement between the retaining mechanism 22 and the cannula member 12 can also allow the retaining mechanism 22 to hold the sections 46a, 46b, 46c in the expanded position (or in any intermediate position between the expanded and retracted positions) against the biasing force supplied by the biasing member 20. Also, when the retaining mechanism 22 is threadably advanced toward the proximal end 32 of the cannula member 12, the tension in the biasing member 20 can cause the sections 46a, 46b, 46c to move parallel to the axis X toward the proximal end 32 and to move radially inward toward the retracted position. The abutment walls 49 of the sections 46a, 46b, 46c can abut against the shoulders 47 to limit axial movement of the sections 46a, 46b, 46c as shown in FIG. 4.

Accordingly, the guide tube 10 can be used, for instance, to guide movement of a neurological probe 30 (FIG. 5) or other similar device toward and away from a target T within the patient's body (e.g., the patient's brain). First, the hole 24 can be formed within the cranial bone or other tissue 28 (FIG. 4). The hole 24 can be formed such that a centerline C of the hole 24 intersects the target T. In some embodiments, the hole 24 can be circular in shape and can have a diameter of six millimeters (6 mm) to ten millimeters (10 mm); however, the hole 24 can have any suitable shape and dimensions.

Then, assuming that the sections 46a, 46b, 46c of the expansion member 18 are positioned in the retracted position (FIG. 4), the sections 46a, 46b, 46c and the distal end 34 of the cannula member 12 can be inserted into the hole 24 such that the proximal end 32 of the cannula member 12 projects therefrom. In some embodiments, the shoulder 51 abuts against the tissue 28 surrounding the hole 24 to limit movement of the guide tube 10 into the hole 24.

Then, the retaining mechanism 22 can be threadably advanced to move the sections 46a, 46b, 46c of the expansion member 18 toward the expanded position, and the outer surfaces 48 of the sections 46a, 46b, 46c can engage with the inner surface 26 of the hole 24. Thus, the guide tube 10 can be fixed relative to the cranial tissue 28, the axis X can be substantially aligned with the centerline C of the hole 24, and the axis X can intersect the target T within the patient.

It will be appreciated that the outer surface 48 of each section 46a, 46b, 46c can remain substantially parallel to the axis X as the sections 46a, 46b, 46c move toward the expanded position. Since the hole 24 can have a substantially constant width along its axis C, the outer surfaces 48 of the sections 46a, 46b, 46c can engage a relatively large surface area of the inner surface 26 of the hole 24. Stated differently, the outer surfaces 48 of the sections 46a, 46b, 46c can have surface contact (as opposed to point contact) with the inner surface 26 of the hole 24. As such, the sections 46a, 46b, 46c of the expansion member 18 can distribute forces substantially evenly to the tissue 28, the guide tube 10 is likely to be very stable when engaged with the tissue 28, and the guide tube 10 is unlikely to fracture or otherwise damage the tissue 28 when engaging the tissue 28.

Next, as shown in FIG. 5, the probe 30 can be inserted within the passage 14, and the inner surface 36 of the passage 14 can help guide the probe 30 as it moves along the axis X toward the probe. After the procedure is completed, the probe 30 can be moved in a reverse direction along the axis X and withdrawn from the guide tube 10. Then, the sections 46a, 46b, 46c can be moved to the retracted position, and the guide tube 10 can be removed from the hole 24.

As shown schematically in FIGS. 3, 4, and 5, the guide tube 10 can include a tracking sensor 71 that can track the position and/or orientation of the guide tube 10 relative to the patient and/or the probe 30. (The tracking sensor 71 is represented schematically by a boxed "S".) For instance, the tracking sensor 71 can be operable for tracking the position and/or orientation of the passage 14 within the cannula member 12 relative to the patient. Although the tracking sensor 71 is shown included on the cannula member 12, the tracking sensor 71 can be included on one or more of the sections 46a, 46b, 46c of the expansion member 18, the retaining mechanism 22, or any other portion of the guide tube 10. The tracking sensor 71 can include features taught in the commonly-owned U.S. patent application Ser. No. 11/739,401 filed Apr. 24, 2007, U.S. patent application Ser. No. 12/103, 488, filed Apr. 15, 2008, U.S. patent application Ser. No. 12/239,114, filed Sep. 26, 2008, and/or U.S. patent application Ser. No. 12/770,181, filed Apr. 29, 2010, each of which is hereby incorporated by reference in its entirety. The tracking sensor 71 can be a coil of conductive material or another instrument that transmits and/or receives electromagnetic signals according to the position and/or orientation of the guide tube 10. The tracking sensor 71 can also be an optical transmitter, reflector, receiver, or another instrument that transmits and/or receives optical signals corresponding to the position and/or orientation of the guide tube 10. The tracking sensor 71 can also employ combinations of these and other tracking technologies. Also, the tracking sensor 71 can operatively communicate with a corresponding sensor 73 that is attached to the probe 30 (FIG. 5). Moreover, the tracking sensor 73 can detect the trajectory of the probe 30, the amount of distance the probe 30 has moved toward and/or away from the guide tube 10, the amount of distance the probe 30 has moved into and/or out of the patient's body, etc.

Other variations of the guide tube 10 are within the scope of the present disclosure. For instance, although the axis X is at a fixed orientation relative to the sections 46a, 46b, 46c of the expansion member 18 in the embodiments discussed above, the guide tube 10 could be configured such that the orientation of the axis X can be varied relative to the expansion member 18 in other embodiments. In the latter case, the guide tube 10 could be engaged with the inner surface 26 of the hole 24 as discussed above, and then the cannula member 12 could be selectively rotated, bent, or otherwise repositioned to reorient the axis X relative to the expansion member 18 and the hole 24. For instance, the guide tube 10 could include multiple sections that are attached by a gimbaled joint, ball-and-socket joint, etc., and the sections could be pivoted relative to each other to reorient the axis X. As such, even if the centerline C of the hole 24 is out of alignment with the target T, then the axis X of the cannula member 12 can be selectively oriented toward the target T. Also, if there are several targets T that can be accessed through one hole 24, the guide tube 10 can remain in the same position on the cranial tissue 28 to access each of the targets T.

It will also be appreciated that the guide tube 10 could be made out of any suitable materials. For instance, in some embodiments, one or more of the components of the guide tube 10 are made out of a polymeric material (e.g., injection molded plastic). As such, the guide tube 10 could be intended for one-time use (i.e., can be disposable). In other embodiments, one or more components could be made of metal, and the guide tube 10 could be intended for multiple uses. In the latter case, the guide tube 10 can be sterilized between uses (e.g., in an autoclave).

In summary, the guide tube 10 can be attached and detached from the patient in a very convenient manner. Also, the guide tube 10 can accurately guide the instrument 30 toward the desired target T within the patient despite the hole 24 having a relatively small width.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A guide tube for guiding an instrument through a hole within tissue of a patient, the hole being defined by a surface, the guide tube comprising:
   a cannula member defining a passage extending therethrough along an axis from a proximal end to a distal end, the passage operable to receive the instrument and guide the instrument through the hole within the tissue of the patient, the cannula member including an exterior surface having a tapered portion adjacent the distal end, the tapered portion increasing in diameter toward the distal end; and
   an expansion member that is moveably coupled to the cannula member to selectively move radially between a retracted position and an expanded position relative to the axis of the cannula member, wherein the expansion member includes a plurality of sections that are spaced circumferentially about the axis and each section remains in slidable surface contact along the tapered portion of the exterior surface to move between the expanded and retracted positions, the expansion member being at least partially insertable into the hole when the expansion member is in the retracted position, the expansion member operable to engage with the surface of the hole when the expansion member is in the expanded position, and wherein the expansion member includes an outer surface that is operable to engage the surface of the hole, the outer surface moving radially toward and away from the axis when moving between the retracted and expanded positions, the outer surface being substantially parallel to the axis in a section of the expansion member taken along the axis as the expansion member moves between the retracted and expanded positions.

2. The guide tube of claim 1, wherein the tapered portion is tapered at an acute angle relative to the axis.

3. The guide tube of claim 2, wherein the tapered portion includes a proximal end and a distal end, wherein the tapered portion is tapered such that a distal radius from the axis at the distal end of the tapered portion is greater than a proximal radius at the proximal end of the tapered portion.

4. The guide tube of claim 2, wherein the plurality of sections are slidable in tandem along the tapered portion of the exterior surface to move between the expanded and retracted positions.

5. The guide tube of claim 1, wherein one of the exterior surface of the cannula and an inner surface of the expansion member includes a groove and the other of the exterior surface of the cannula and the inner surface of the expansion member includes a rail that is slidably received in the groove for guiding movement between the expanded and retracted positions.

6. The guide tube of claim 2, wherein the expansion member is biased toward one of the retracted position or the expanded position, and further comprising a retaining mechanism that selectively retains the expansion member in the other of the retracted position or the expanded position.

7. The guide tube of claim 6, wherein the retaining mechanism is threadably attached to the cannula member, the retaining mechanism operable to threadably advance relative to the cannula member to slide the expansion member along the exterior surface of the cannula member to move the expansion member toward the expanded position and retain the expansion member in the expanded position.

8. The guide tube of claim 7, wherein the exterior surface of the cannula member includes an outer threading and the retaining mechanism includes an inner threading that threadably attaches to the outer threading, the retaining mechanism operable to threadably advance in a direction parallel to the axis to slide the expansion member along the tapered portion of the exterior surface of the cannula member.

9. The guide tube of claim 1, further comprising a biasing member that biases the expansion member toward the retracted position.

10. The guide tube of claim 1, wherein the expansion member is operable to substantially align the axis of the passage with a centerline of the hole when the expansion member is in the expanded position.

11. The guide tube of claim 1, wherein the axis is substantially straight.

12. The guide tube of claim 1, wherein the axis is at a fixed orientation relative to the expansion member.

13. The guide tube of claim 5, wherein the rail and the groove are tapered relative to the axis.

14. The guide tube of claim 1, wherein at least one of the cannula member or the expansion member includes a shoulder that abuts against the other of the cannula member or the expansion member to limit movement of the expansion member relative to the cannula member when moving between the retracted and extended positions.

15. The guide tube of claim 1, further comprising a tracking sensor that detects at least one of a position and an orientation of the cannula member relative to the patient.

16. A guide tube for guiding a neurological instrument through a hole formed within a cranium of a patient, the hole being defined by an inner surface, the guide tube comprising:
a cannula member defining a passage extending therethrough along an axis, the passage operable to receive the neurological instrument and guide the instrument through the hole;
an expansion mechanism that includes a plurality of sections having corresponding inner tapered rails slidably attached to corresponding tapered grooves of a tapered portion of an exterior surface of the cannula member, the plurality of sections configured to slide in surface contact along the tapered portion of the exterior surface to thereby move radially relative to the axis between a retracted position and an expanded position, the plurality of sections defining an outer surface that remains substantially parallel to the axis along a section including the axis between the expanded and retracted positions;
a biasing member that is operably coupled to each of the plurality of sections to bias the plurality of sections toward the axis to bias the plurality of sections toward the retracted position; and
a retaining mechanism that is threadably attached to the cannula member, the retaining mechanism being operable to threadably advance relative to the cannula member to slide the plurality of sections along the tapered portion of the exterior surface of the cannula member to move the plurality of sections toward the expanded position, the retaining mechanism also operable to retain the plurality of sections in the expanded position to engage with the inner surface of the hole.

* * * * *